US009809467B2

United States Patent
Lichi et al.

(10) Patent No.: US 9,809,467 B2
(45) Date of Patent: Nov. 7, 2017

(54) SYSTEM AND METHOD FOR INACTIVATION OF INFECTIOUS PANCREATIC NECROSIS VIRUS (IPNV) USING MEDIUM PRESSURE ULTRAVIOLET (UV) LIGHT

(71) Applicant: Atlantium Technologies Ltd., Beit-Shemesh (IL)

(72) Inventors: Tovit Lichi, Gedera (IL); Michael Kertser, Bney Aish (IL); Ytzhak Rozenberg, Ramat Gan (IL)

(73) Assignee: Atlantium Technologies Ltd, Beit-Shemesh (IL)

( * ) Notice: Subject to any disclaimer, the term of this patent is extended or adjusted under 35 U.S.C. 154(b) by 346 days.

(21) Appl. No.: 14/362,132

(22) PCT Filed: Mar. 13, 2014

(86) PCT No.: PCT/IL2014/050269
§ 371 (c)(1),
(2) Date: Jun. 2, 2014

(87) PCT Pub. No.: WO2014/141269
PCT Pub. Date: Sep. 18, 2014

(65) Prior Publication Data
US 2016/0107903 A1 Apr. 21, 2016

Related U.S. Application Data

(60) Provisional application No. 61/788,477, filed on Mar. 15, 2013.

(51) Int. Cl.
*A61L 2/00* (2006.01)
*C02F 1/32* (2006.01)
*A61L 2/10* (2006.01)

(52) U.S. Cl.
CPC ............... *C02F 1/325* (2013.01); *A61L 2/10* (2013.01); *C02F 1/32* (2013.01); *C02F 2303/04* (2013.01)

(58) Field of Classification Search
CPC .................................. A61L 2/10; C02F 1/325
See application file for complete search history.

(56) References Cited

U.S. PATENT DOCUMENTS

| | | | |
|---|---|---|---|
| 2004/0232358 A1* | 11/2004 | Moruzzi | A23L 3/28 250/504 R |
| 2008/0206095 A1 | 8/2008 | Duthie | |
| 2011/0226966 A1 | 9/2011 | Takahashi et al. | |

FOREIGN PATENT DOCUMENTS

| WO | WO 2007/113537 | 10/2007 |
|---|---|---|
| WO | WO 2008/059503 | 5/2008 |
| WO | WO 2010/071814 | 6/2010 |

OTHER PUBLICATIONS

Helge Liltved et al. "Inactivation of bacterial and viral fish pathogens by ozonation or UV irradiation in water of different salinity", Aquacultural engineering, Jan. 1, 1995, vol. 14, No. 2, pp. 107-122, 119.

(Continued)

*Primary Examiner* — Kevin Joyner
(74) *Attorney, Agent, or Firm* — Pearl Cohen Zedek Latzer Baratz LLP (57) ABSTRACT

A method and a system is provided for inactivation of Infectious Pancreatic Necrosis Virus (IPNV) comprising illuminating a liquid containing IPNV with a lamp emitting a continuous broad band of ultraviolet (UV) light. The UV lamp may be "tuned" to optimize IPNV inactivation. The lamp may be a medium pressure UV lamp that emits UV light having wavelength between 260-400 nm and preferably, between 260-300 nm. The pressure of the lamp may be (Continued)

greater than 1.6 bar, 3 bar and preferably is 7 bar. The lamp may be composed of PS (synthetic quartz).

6 Claims, 9 Drawing Sheets

(56) References Cited

OTHER PUBLICATIONS

Liltved H et al. "High resistance of fish pathogenic viruses to UV irradiation and ozonated seawater", Aquacultural engineering, Mar. 1, 2006, vol. 34, No. 2, pp. 72-82.
Lakretz et al., "Biofouling control in water by various UVC wavelengths and doses", Biofouling, Apr. 2010, pp. 257-267, vol. 26, No. 3.
Bolton et al., "Standardization of methods for fluence (UV dose) determination in bench-scale UV experiments.", J. Environ. Eng. ASCE 129, Mar. 2003, pp. 209-215.
Reed, L.J., & Muench, H. "A Simple Method of Estimating Fifty Per Cent Endpoints", The American journal of Hygiene, May 1938, vol. 27, No. 3, pp. 493-497.
Ultraviolet Disinfection Guidance Manual for the Final Long Term 2 Enhanced Surface Water Treatment Rule, Nov. 2006, EPA United States Environmental Protection Agency.
Patent Cooperation Treaty Search report for international application PCT/IL2014/050269 dated Jun. 2, 2014.

\* cited by examiner

Action spectrum for the inactivation of IPNV with UV light

| | |
|---|---|
| 220 | 17.04808 |
| 239 | 2.423077 |
| 254 | 1 |
| 260 | 1.721154 |
| 280 | 3.134615 |

SYSTEM AND METHOD FOR INACTIVATION OF INFECTIOUS PANCREATIC NECROSIS VIRUS (IPNV) USING MEDIUM PRESSURE ULTRAVIOLET (UV) LIGHT

CROSS-REFERENCE TO RELATED APPLICATIONS

This application is a National Phase Application of PCT International Application No. PCT/IL2014/050269, International Filing Date Mar. 13, 2014, claiming priority of U.S. Provisional Patent Application No. 61/788,477, filed Mar. 15, 2013 which is hereby incorporated by reference.

BACKGROUND

Infectious Pancreatic Necrosis Virus (IPNV) is a common contaminant in water and other liquids in fish farms and is suspected of depleting populations of salmon species, such as, Norwegian and Chilean salmon. Ultraviolet (UV) light may be used to disinfect contaminated liquid to inactivate IPNV and thus, reduce the risk of illness. To effectively decontaminate liquid, IPNV may be inactivated to a degree greater than or equal to a log value of 3 ($\geq$99.9% inactivation) by radiating with a standard low pressure UV lamp at a wavelength of 254 nm and applying at least a UV dose of around 250 mJ/cm$^2$. Since the UV dose needed for inactivation is relatively high, standard UV lamps use relatively high amounts of electricity to achieve effective decontamination.

SUMMARY

Embodiments of the invention provide a system, device and method for using a UV lamp "tuned" to optimize IPNV inactivation. In tests carried out according to embodiments of the invention, lamps having a wavelength above 260 nanometers (nm) and/or below 245 nm were found to inactivate IPNV, e.g., between 3 and 70 times more than UV light at 254 nm or more accurately at 253.7 nm. The value of 254 nm, as used herein refers to the current commonly used industrial LP lamps, which emit at the wavelength of 253.7 nm. Water transmission is better in the high range (e.g. above 260 nm) than the low range (e.g. below 245 nm). Further, polychromatic (medium pressure) UV lamps substantially in a wavelength range between 260 and 400 nm were discovered to inactivate IPNV using significantly less UV light or UV dose than monochromatic (low pressure) UV lamps emitting in 253.7 nm.

In some embodiments of the invention, a liquid containing IPNV may be illuminated with a spectrally optimized medium pressure UV light in a UV dose level of less than approximately 50% compared to a UV dose level of a low pressure lamp emitting at 253.7 nm to produce the same level of log inactivation of IPNV. Accordingly, spectrally optimized medium pressure lamp requires less electricity to produce the same level of inactivation level. The lower UV dose level the less electricity required. Optimized IPNV customized lamps are lamps customized and designed based on the response sensitivity of the IPN virus. Based on the response sensitivity of the IPN virus, higher pressure optimized MP lamps may contribute more to a cumulative intensity than the lower pressure MP lamp. Embodiments of the invention include a MP lamp with pressure higher than 1.6 bar and preferably, higher than 4 or 5 bar so as to match the spectral response of the IPN virus to UV light.

In some embodiments, a UV lamp "tuned" to optimize IPNV inactivation may be a medium pressure polychromatic UV lamp that emits UV light substantially in a wavelength range of between 260 and 400 nm. In some embodiments, the UV lamp may be a medium pressure UV lamp that emits UV light substantially in a wavelength range of between 260 and 300 nm. The "tuned" medium pressure polychromatic UV lamp may have a pressure above 1.6 bar, for example above 3 bar, above 5 bar, above 6 bar etc. In other embodiments, the UV lamp may be a monochromatic lamp that emits UV light having a single wavelength in the range of 260-400 nm and preferably, in the range of 260-300 nm.

In some embodiments, a UV lamp "tuned" to optimize IPNV inactivation may be a medium pressure polychromatic UV lamp that emits UV light substantially in a wavelength range of between 200 and 245 nm. In some embodiments, the UV lamp may be a medium pressure UV lamp that emits UV light substantially in a wavelength range of between 200 and 220 nm. The "tuned" medium pressure polychromatic UV lamp may have a pressure above 1.6 bar, for example above 3 bar, above 5 bar, above 6 bar etc. In other embodiments, the UV lamp may be a monochromatic lamp that emits UV light having a single wavelength in the range of 200-245 nm and preferably, in the range of 200-220 nm.

Both polychromatic and monochromatic UV lamp in both the upper and lower wavelength ranges are referred to herein as "IPN customized UV lamp". The IPN customized UV lamps according to embodiments of the invention may be composed of pure silica synthetic quartz (PS)

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

It will be appreciated that for simplicity and clarity of illustration, elements shown in the figures have not necessarily been drawn to scale. For example, the dimensions of some of the elements may be exaggerated relative to other

DETAILED DESCRIPTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "processing," "computing," "calculating," "determining," or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

In some embodiments of the invention, a UV lamp is provided that is optimized to inactivate IPNV. The UV lamp may be a medium pressure UV lamp that emits UV light substantially in a wavelength range of between 260 and 400 nm. In some embodiments, the UV lamp may be a medium pressure UV lamp that emits UV light substantially in a wavelength range of between 260 and 300 nm.

Disinfection systems may irradiate liquids with UV light to reduce or inactivate IPNV. UV lamps may be monochromatic or polychromatic. Monochromatic lamps emit a single wavelength of UV light (for example, 280 nanometers (nm)). Throughout the specification, only the commonly used monochromatic UV lamps that emit at around 254 nm are referred to as "low pressure" (LP) UV lamps. Polychromatic lamps emit multiple wavelengths of UV light, for example, in discrete increments or in a continuous broad band range (e.g., 260-300 nm), and may be referred to as "medium pressure" (MP) UV lamps. In tests carried out according to embodiments of the invention, optimally customized medium pressure (MP) UV lamps were discovered to inactivate IPNV at significantly greater rates than standard low pressure (LP) UV lamps configured to emit at 253.7 nm. Since the standard LP and customized MP UV lamps inactivate IPNV at different rates, the proper UV intensity and UV exposure time, i.e., the "UV dose," to decontaminate liquid may differ for each of the lamps.

Measuring the UV dose may be simple for a LP UV lamp (e.g., using equation $D_{CB}$ defined below) since illumination exposure parameters may be easily measured for the single wavelength of the monochromatic UV light. However, this calculation may not be used for polychromatic light. MP UV lamps, which radiate light over multiple wavelengths, include some wavelengths that actively reduce IPNV, and other wavelengths that are innocuous or less effective at reducing IPNV. To accurately determine the intensity of MP light, the intensity may be measured separately at each of the active wavelengths, a generally difficult task. Currently, only the UV dose to disinfect IPNV with a standard LP UV lamp emitting at 253.7 nm is known, while the UV dose for MP light remains unknown.

To accurately calculate the intensity or UV dose of MP UV light, which may be difficult to measure directly, embodiments of the invention may measure the UV dose using an LP UV light that gives an equivalent (of near equivalent) reduction in microorganisms. Such an MP UV dose may be referred to as a "reduction equivalent" UV dose (RED) since it is not measured, but determined to be equivalent to a LP UV dose that achieves a similar reduction. In one embodiment, to determine the reduction equivalent UV dose for MP radiation of IPNV, the LP UV dose may be measured, not for IPNV, but for another control organism, such as, male specific-2 bacteriophage (MS2). The control organism may have a known correlation between the LP UV doses and the reduction equivalent MP UV doses used to inactivate the same amounts of the control organism. MS2 is inactivated in equivalent UV doses by LP and MP UV light, although other control organisms with non-equivalent LP and MP UV doses may also be used, as long as the correlation between their LP and MP UV doses is known or measurable.

In one example, the MP UV dose used to achieve at least a 3 log (≥99.9%) reduction of IPNV was determined to be at least 50% lower compared to a UV dose level of a low pressure lamp emitting at 253.7 nm. (LP UV dose) For comparison, the LP UV dose used to achieve the same reduction in IPNV is approximately 120-246 mJ/cm². Thus, MP lamps provide the same reduction as LP lamps, but with such a significantly smaller UV dose, for example, at least 3-5 times less than LP lamps. Whereas there is substantially no difference between radiating MS2 with MP and LP UV light, such a significant difference between radiating IPNV with MP and LP UV light provides a unique and unexpected result.

Figure 1:
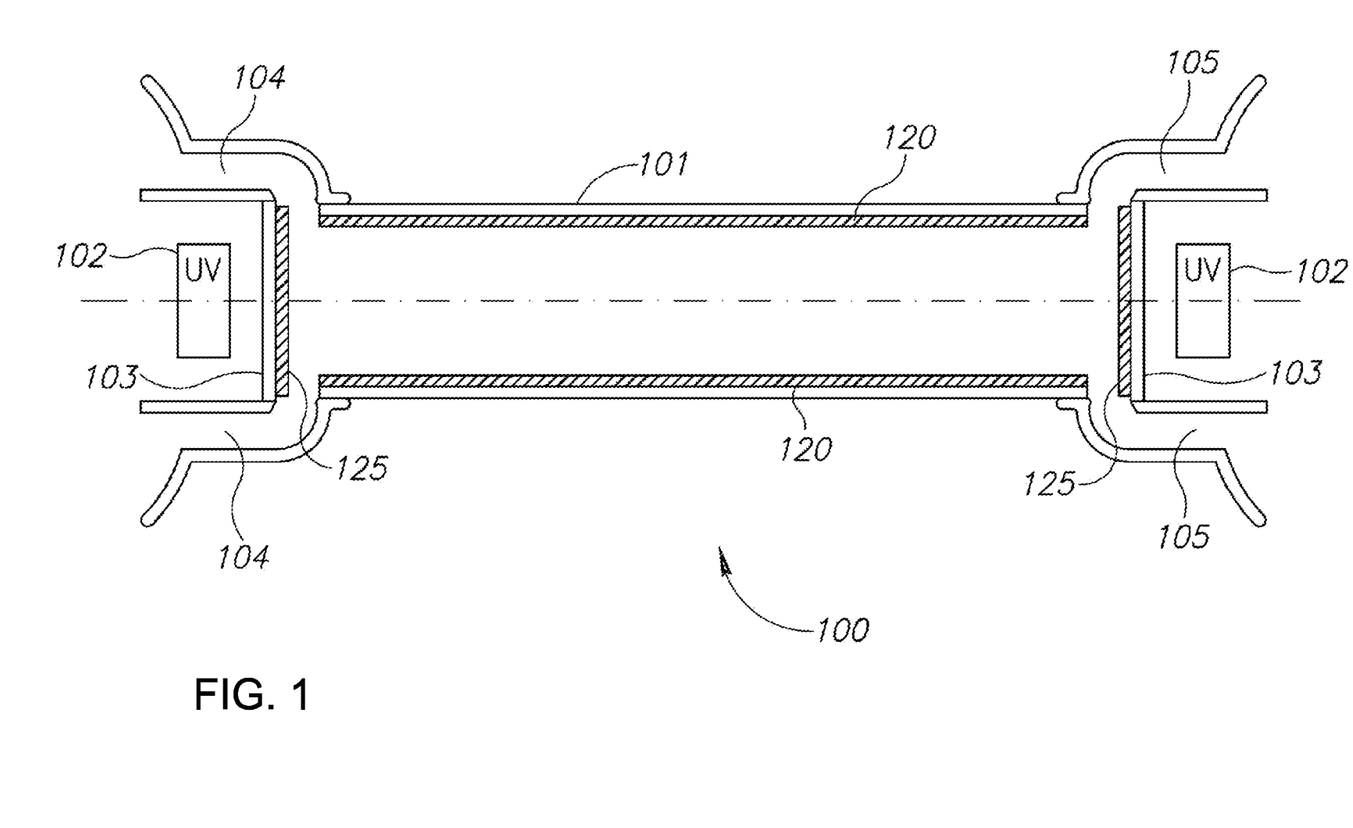
FIGS. 1 and 2 schematically illustrate systems for disinfecting a liquid containing in accordance with embodiments of the invention.
Figure 2:
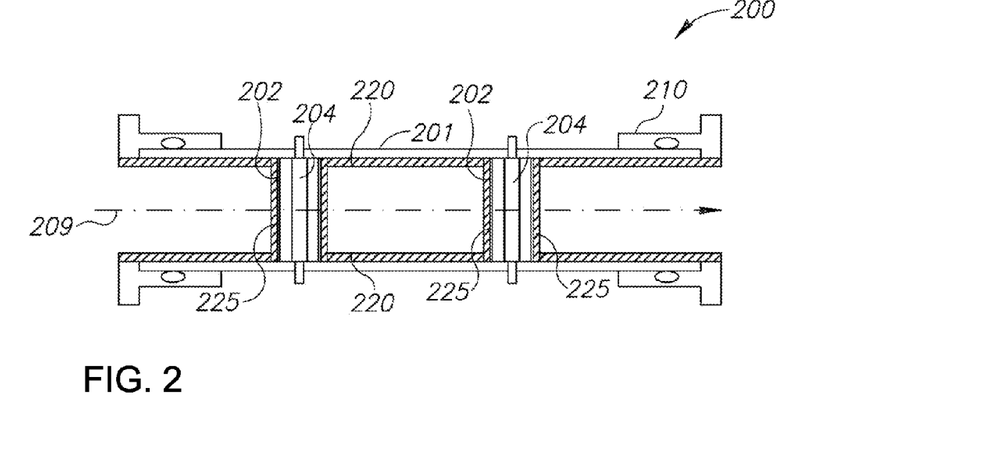

Reference is made to FIGS. 1 and 2, which schematically illustrate systems 100 and 200 for disinfecting a liquid containing IPNV in accordance with embodiments of the invention. FIG. 1 includes UV sources 102 positioned externally to conduit 101 and FIG. 2 includes UV sources 204 positioned internally to conduit 201 within the cavity of the channel, although any arrangement or combination of internal and/or external UV sources may be used.

In FIG. 1, system 100 may include a tube, channel or conduit 101 to carry flowing liquid to be disinfected and one or more external UV sources 102 to illuminate and to disinfect the liquid within conduit 101. Conduit 101 may have an inlet 104 to receive the liquid, and an outlet 105 to discharge the liquid. Conduit 101 may be made, at least partially, of a UV transparent material, such as glass or quartz. System 100 may include one or more windows 103 which may be made of UV transparent material, such as glass or quartz and may, for example, be coated with an anti-deposit layer 125.

UV sources 102 may illuminate or irradiate the liquid when flowing in conduit 101 to inactivate contaminants, such as, IPNV. In some embodiments, the liquid within conduit 101 may act as a waveguide and at least part of the light, for example, at least half of the emitted UV intensity, may be totally-internally reflected at the interface of the UV-transparent conduit 101 and the surrounding air. UV sources 102 may include one or more IPN customized UV lamp, for example medium pressure UV sources, adapted to emit polychromatic light at multiple (discrete or continuous) wavelengths (e.g., in a range throughout the germicidal UV range and beyond). UV source 104 may comprise pure silica synthetic quartz (PS) UV sources 102 may emit UV light substantially in a wavelength range of between 200 and 245 nm. In some embodiments, the UV lamp may be a medium pressure UV lamp that emits UV light substantially in a wavelength range of between 200 and 220 nm. The "tuned" medium pressure polychromatic UV lamp may have a pressure above 1.6 bar, for example above 3 bar, above 5 bar, above 6 bar etc. In other embodiments, UV source 102 may be a monochromatic lamp that emits UV light having a single wavelength in the range of 200-245 nm and preferably, in the range of 200-220 nm.

UV sources 102 may be set to emit UV light at a fixed UV dose predetermined (e.g., in the testing phase of FIG. 3) to inactivate IPNV by an optimal degree. For example, medium pressure UV sources 102 may illuminate liquid with a UV dose of less than or equal to 80 mJ/cm$^2$ to achieve an inactivation of IPNV by at least a 3 log values (99.9%).

In FIG. 2, system 200 may include a conduit 201 to carry flowing liquid to be disinfected and one or more internal UV sources 204 to illuminate and to disinfect the liquid within conduit 101. An illuminating surface of each UV source 204 may be substantially perpendicular to a longitudinal axis of symmetry 209 of conduit 201, such that the direction of illuminating rays is parallel to longitudinal axis of symmetry 209. UV source 204 may comprise pure silica synthetic quartz (PS). UV source 204 may emit UV light substantially in a wavelength range of between 200 and 245 nm. In some embodiments, the UV lamp may be a medium pressure UV lamp that emits UV light substantially in a wavelength range of between 200 and 220 nm. The "tuned" medium pressure polychromatic UV lamp may have a pressure above 1.6 bar, for example above 3 bar, above 5 bar, above 6 bar etc. In other embodiments, UV source 102 may be a monochromatic lamp that emits UV light having a single wavelength in the range of 200-245 nm and preferably, in the range of 200-220 nm. Each UV source 204 may be positioned in a UV-transparent sleeve 202. Sleeve 202 may comprise pure silica synthetic quartz (PS).

In the examples shown in FIGS. 1 and 2, systems 100 and 200 are flow systems that disinfect liquid as it passes through conduits 101 and 201, respectively, although systems 100 and 200 may be configured in any other arrangement, such as, a movable UV source passing through a closed container of liquid, a UV source with sufficient surface area to irradiate an entire liquid sample so that no relative motion is needed to expose all the liquid, etc.

Figure 3:
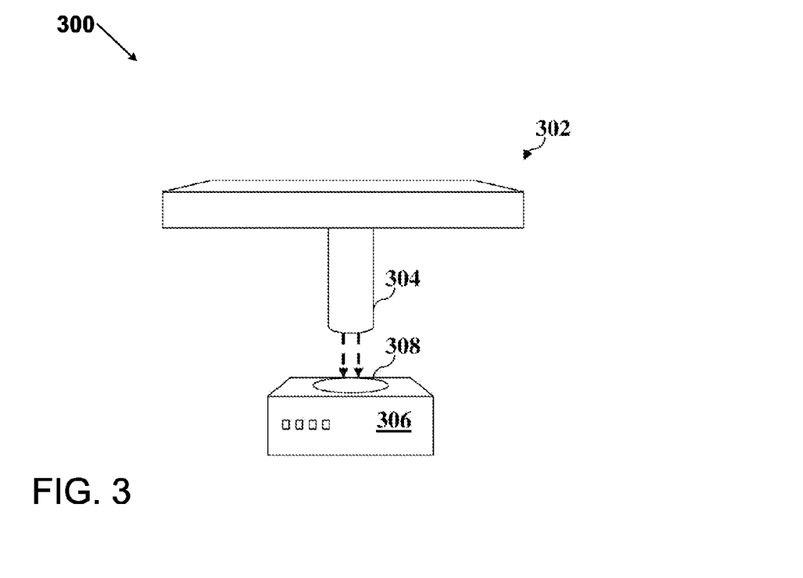
FIG. 3 schematically illustrates a system for determining the biological response of IPNV to UV light in accordance with embodiments of the invention.
Figure 4:
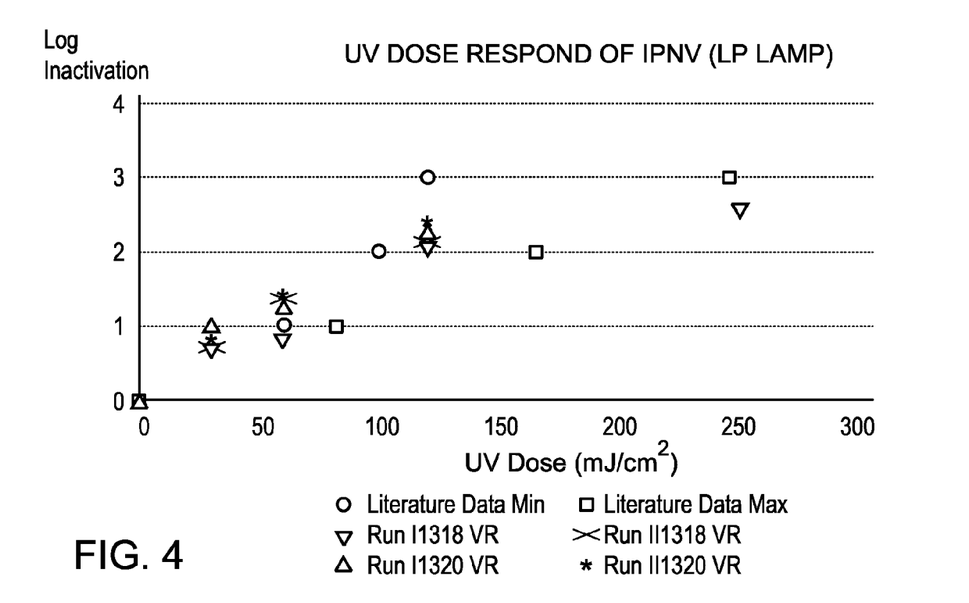
FIG. 4 is a graph that plots the correlation between UV doses for low and medium pressure UV light, respectively, and the inactivation of IPNV, in accordance with embodiments of the invention.
Figure 5:
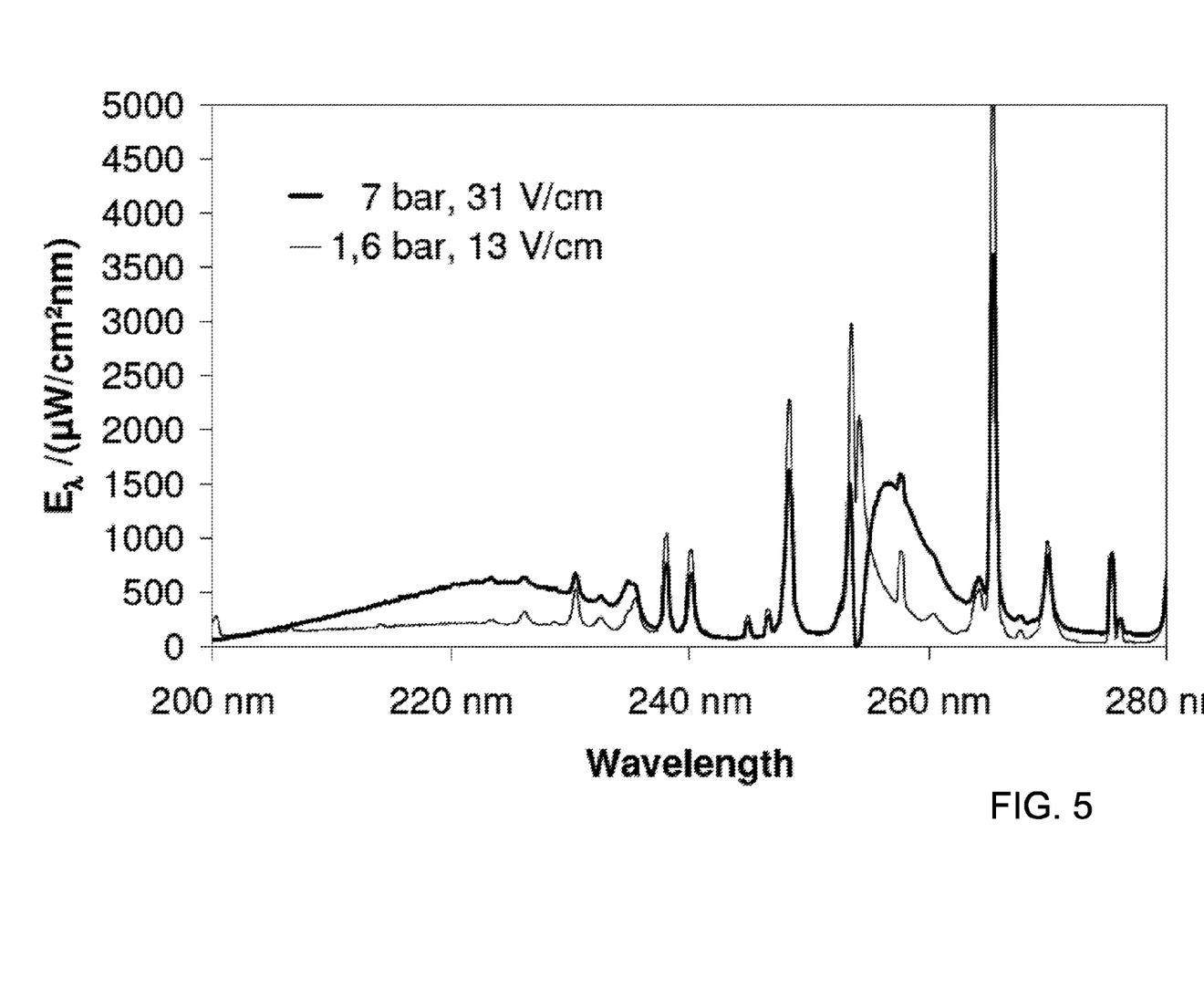
FIG. 5 is a graph of the relative spectra of MP UV lamps at different pressures (e.g., defined by mercury (Hg) bars)
Figure 6:
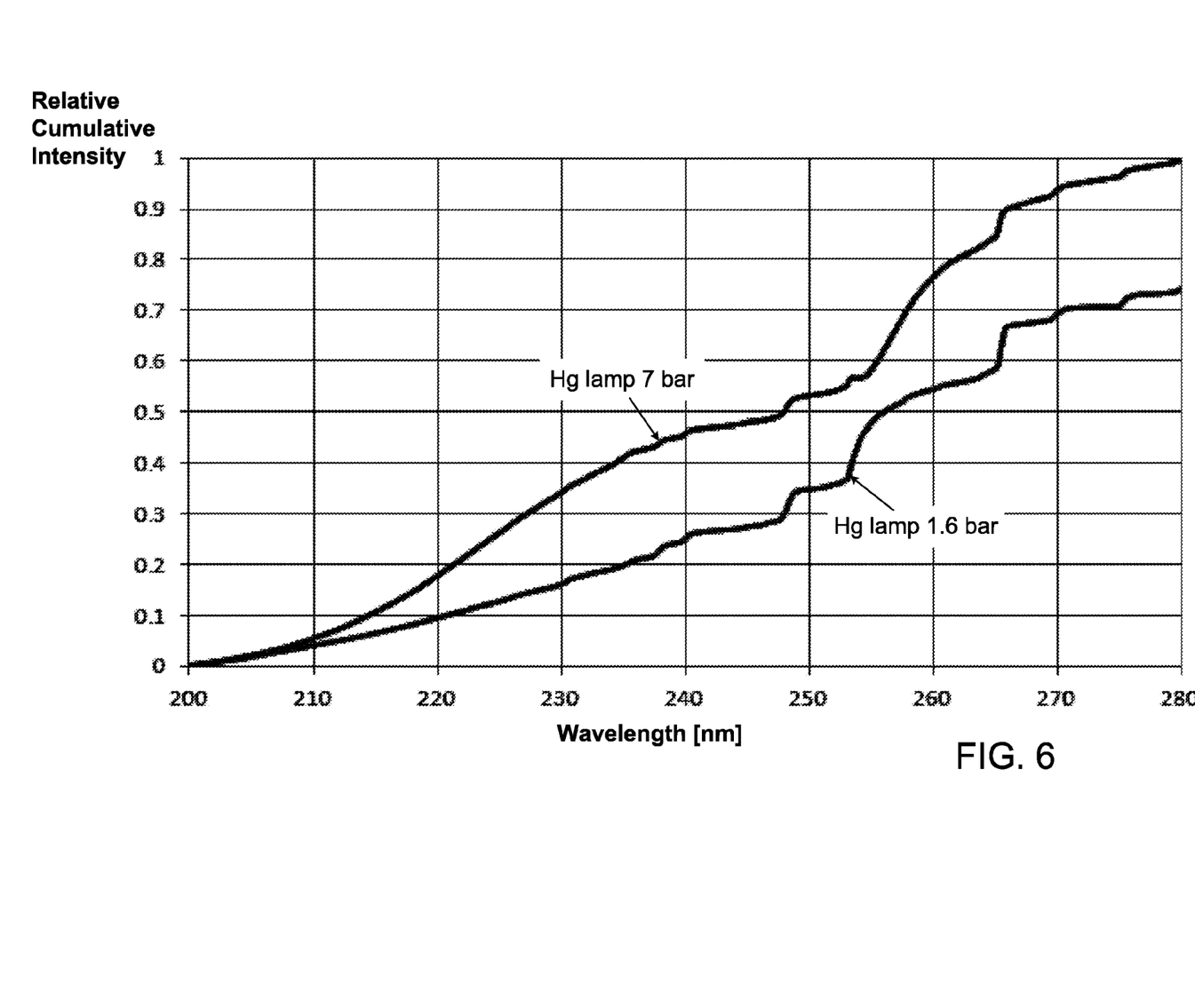
FIG. 6 is a graph of the cumulative intensity of the MP lamps with different pressures.
Figure 7:
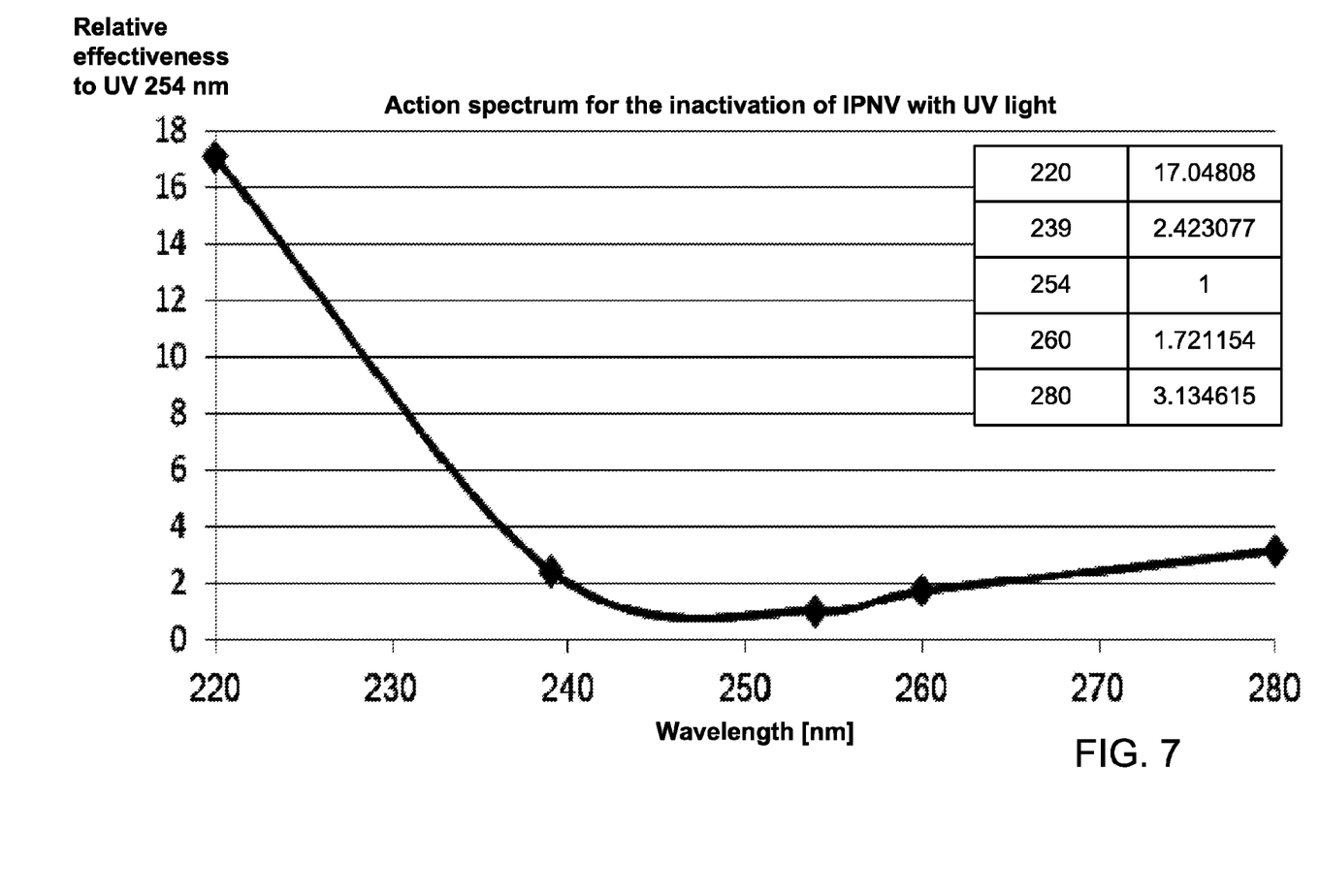
FIG. 7 is a graph of the IPN spectral response curve, normalized at 254 nm.
Figure 8:
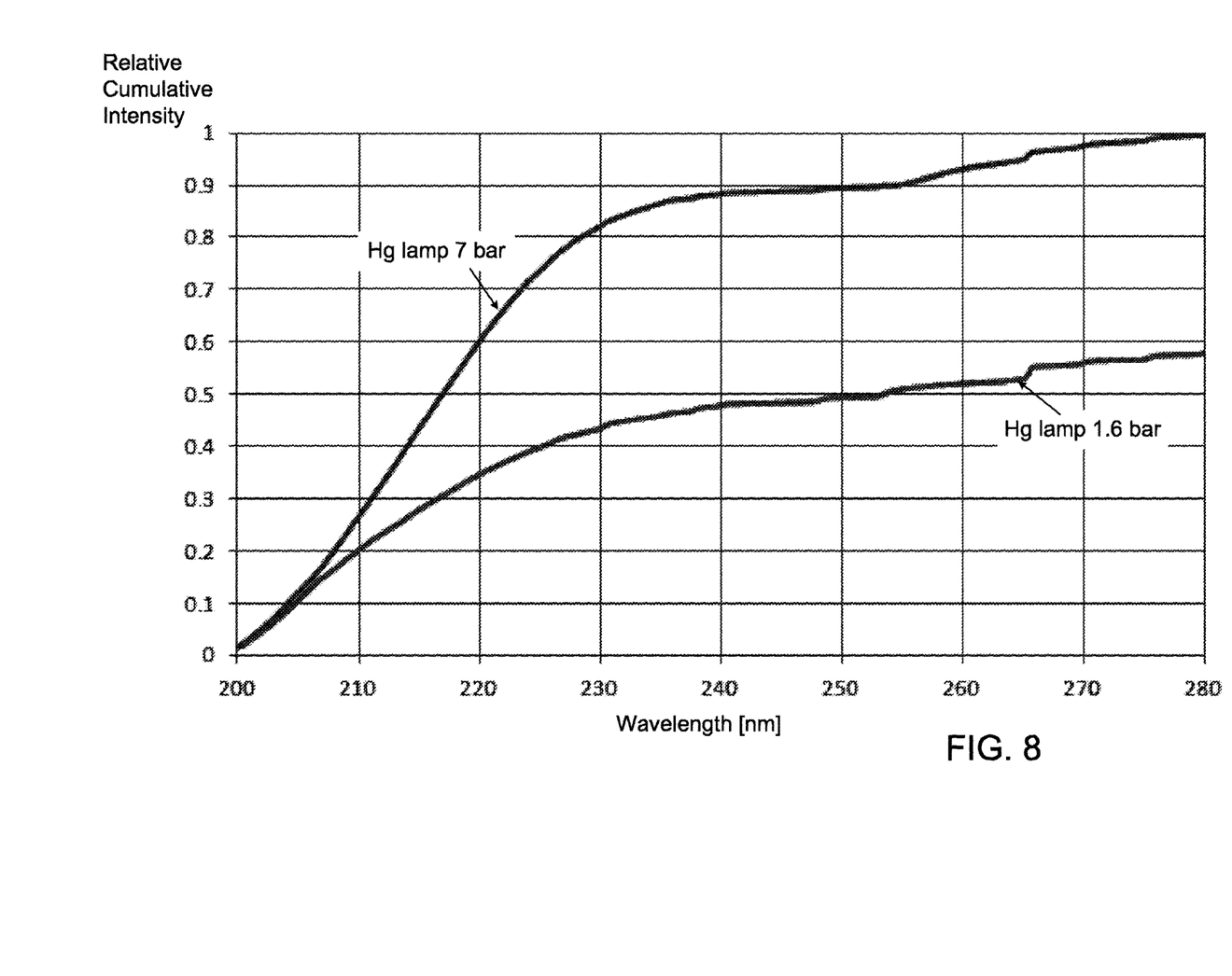
FIG. 8 is a graph of the cumulative intensity of the MP lamps with different pressures with respect to the IPN spectral response.
Figure 9:
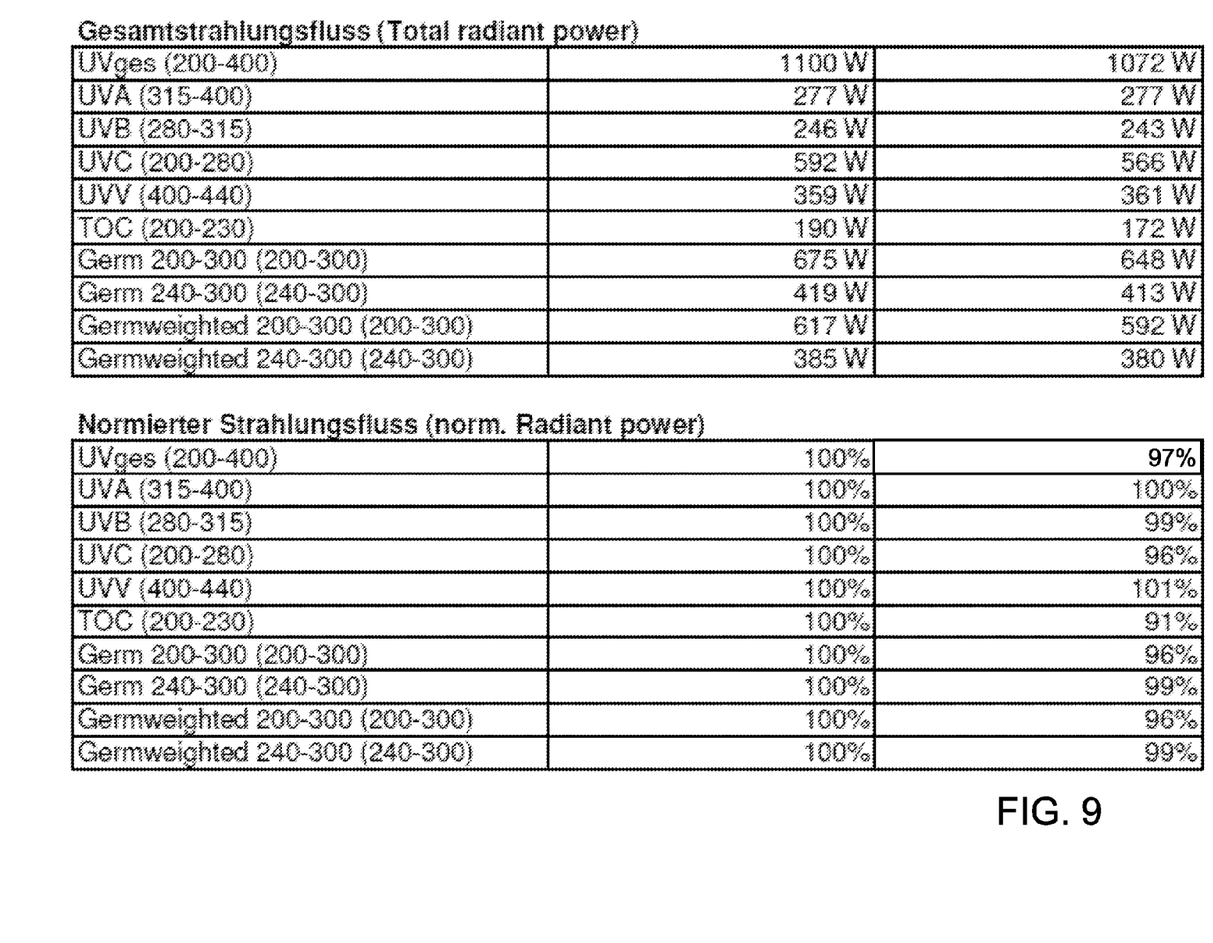
FIG. 9 is a summary table listing the total radian power and normalized radian power of a PS (synthetic quartz) MP lamp and a regular quartz MP lamp.
Figure 10:
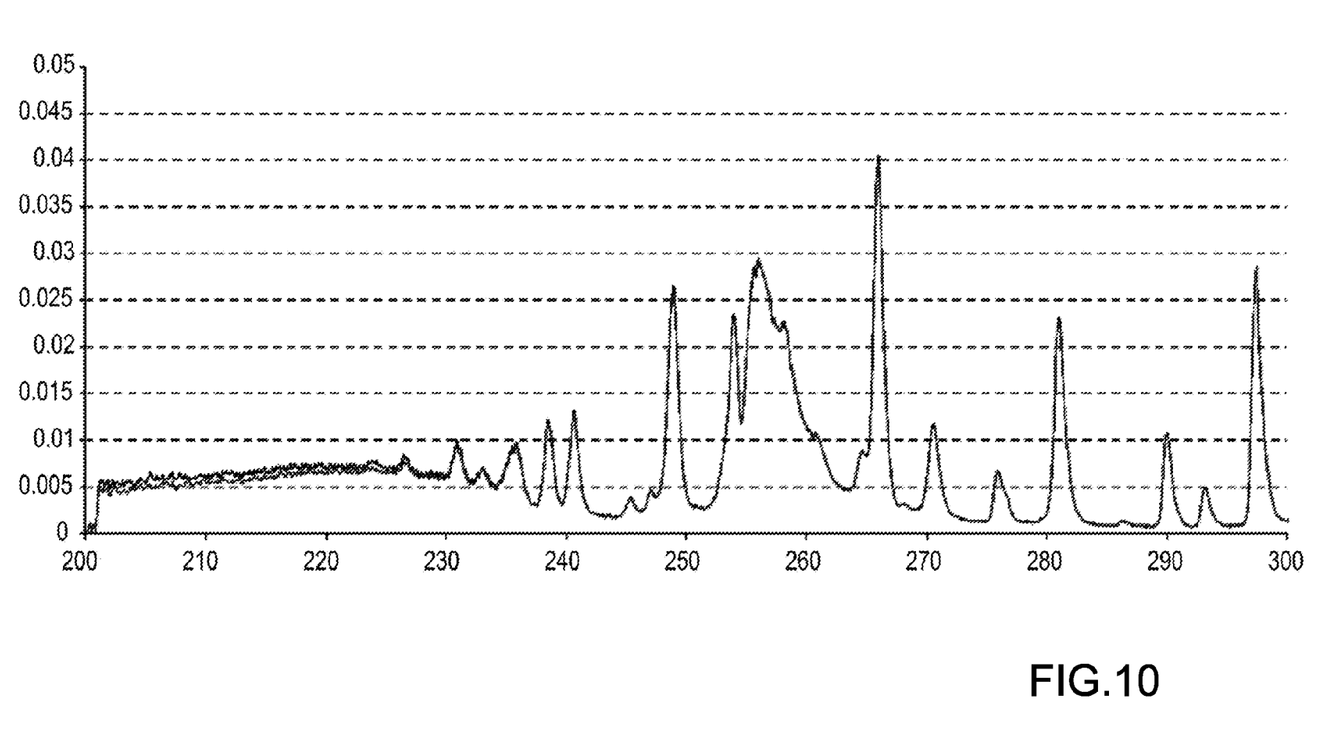
FIG. 10 is a graph of the spectra of a PS (synthetic quartz) MP lamp (violet), and the regular quartz (blue).

Reference is made to FIG. 3, which schematically illustrates a bio-dosimetry system 300 for determining the biological response of IPNV to UV light in accordance with embodiments of the invention.

System 300 may include a collimated beam apparatus 302 with a UV source 304 and a detector 306 which may include a magnetic stirrer. Samples 308 of liquid contaminated with known quantities of microorganisms are positioned between the UV source 304 and detector 306 to test their response to UV doses of low and/or medium pressure light from UV sources 304. Samples 308 may include aliquots of mixed cultures, e.g., placed in Petri dishes, including IPNV and a control organism, such as, MS2, tested separately.

The IPNV sample 308 may be exposed to medium pressure UV source 304 for various exposure conditions, such as, various intensities and/or exposure times, and collimated beam apparatus 302 may measure the concentration of inactive (or active) IPNV for each of these exposures. Collimated beam apparatus 302 may measure the IPNV inactivation concentrations corresponding to each set of exposure conditions. Exposures conditions above a certain intensity and/or duration may inactivate IPNV by an optimal concentration (e.g., by at least log 3). Although the exposure conditions are known, the corresponding medium pressure UV doses may not be easily calculated directly due to the spectral spread of polychromatic light.

To deduce the medium pressure UV doses, the UV dose-response may be tested for a control organism with a known correlation between MP and LP UV doses.

For example, MS2 inactivates by substantially similar amounts when exposed to the same MP and LP UV doses. The control organism may be exposed to a variety of medium pressure UV light to determine a correlation between IPNV and the control organism inactivation concentrations for the same exposure settings. The control organism may also be exposed to a variety of low pressure UV light to determine a correlation between LP UV doses and inactivation concentrations of the control organism.

The correlation between IPNV and the control organism inactivation concentrations for each set of MP exposure conditions may be used to correlate MP exposure conditions (linked to IPNV inactivation concentrations) and LP UV doses or their same reduction equivalent MP UV doses (linked to MS2 inactivation concentrations). Accordingly, the MP UV doses for IPNV may be deduced from easily measurable LP UV doses for the control organism. The optimal range of MP UV doses for IPNV may include the subset of those doses that correspond to exposure conditions that inactivate IPNV by an optimal degree (e.g., a log 3 reduction).

Tests were conducted according to embodiments of the invention using a low pressure collimated beam apparatus (LP-CBA) including a low pressure UV lamp measuring the LP UV dose-response for the control organism and IPNV (relating LP UV dose to log inactivation) and, similarly, optimized medium pressure collimated beam apparatus (MP-CBA) including a medium pressure UV lamp measuring the MP UV dose-response for the control organism and IPNV (relating medium pressure exposure settings to log inactivation). Each of the medium and low pressure CBA tests may be preformed, in parallel (e.g., the MS2 and IPNV samples were exposed to the same light at the same exposure time), for the control organism and IPNV to calculate their UV dose responses to the same exposure conditions. The log-inactivation values of IPNV from the MP-CBA were input into the laboratory derived-UV dose-response relationship (CBA test) of the control organism to estimate the reduction equivalent dose (RED) of IPNV delivered by the MP-CBA.

The UV dose calculation spectral respond tests is based on tests described in A. Lakretz et al. 2010 (Anat Lakretz; Eliora Z. Ron; Hadas Mamane; Biofouling control in water by various UVC wavelengths and doses; Biofouling Vol. 26, No. 3, April 2010, (57-267) with slight modifications as follows: The integrated average irradiance between 200 and 300 nm is calculated according to Bolton and Linden (2003) [Bolton J R, Linden K G. 2003. Standardization of methods for fluence (UV dose) determination in bench-scale UV experiments. J Environ Eng ASCE 129:209-215] using the spectral incident irradiance obtained from a calibrated spectroradiometer (USB4000, Ocean Optics) placed in the same x, y position as the center of the crystallization dish and at the surface of the liquid suspension, the water spectral absorbance obtained via a UV-Vis spectrophotometer (Secoman Uvikon xs), the reflection at the sample surface and the measured Petri factor for the dish. The UV influence is calculated by multiplying the average irradiance with exposure time. In addition, band-pass (BP) filters placed in the polychromatic light path will be used to transmit a well-defined band of light from the polychromatic MP light source at a central wavelength of 220, 239, 254, 260 and 280 nm with an average full width at half maximum (FWHM) of 20-27.5 nm and minimum peak transmittance ranges between 12 and 15% (Andover Corporation, NH, USA). The transmission curves for the BP filters, were performed with a UV-Vis spectrophotometer (Cary Bio100, Varian, Inc., Palo Alto, Calif., USA) for absorbance measurement, equipped with a 150 mm diameter IS attachment (Diffuse Reflectance accessory (DRA)-CA-3330, Labsphere, NH, USA). The filter was placed in a holder at the sample transmission port of the integrating sphere. The actual average irradiance, to which the IPNV are exposed when the filters are used, is obtained by multiplying (weighting) the spectral incident irradiance (measured without filters) by the bandwidth at each wavelength (spectral transmittance in percentage), taking into consideration the water spectral absorbance, petri factor and the water reflection.

Different strains of IPNV, American Type Culture Collection (ATCC) #VR-1318 isolated from Trout and ATCC #VR-1320 isolated from Pike fry (*Esox lucius*), were tested to demonstrate the common response of different forms of IPNV to medium pressure UV doses. Both strains of IPNV were propagated in cell cultures including Blugill Fin cell (BF-2) and Chinook Salmon Embryo cell (CHSE-214) cultures. Cell cultures were grown in Minimum Essential Medium Eagle (MEM-Eagle) formulations with non-essential amino acids supplemented with 10% New-born Calf Serum (NBCS), 2 mM L-glutamine, 5% Pen/Strep solution and maintained in a 22-24° Celcius (° C.) CO2 free incubator. Confluent cultures were infected with IPNV and incubated for 4-6 days at 15-16° C. Once extensive cytopathic effect (CPE) was evident in the cells, the medium was collected, aliquoted and maintained at −70° C. for further use. Cells were seeded in 96 well plates, for CHSE-214 $5\times10^4$ cells/well and for BF-2—$8\times10^4$ cells/well. Virus samples were serially 10 fold diluted up to $10^{-8}$ dilutions and used to infect cell monolayers with each dilution assayed in triplicates. Infected cultures were cultivated MEM-Eagle with non-essential amino acids supplemented with 10% NBCS, 2 mM L-glutamine and 20 mM Hepes, at 15-16° C. Four days after infection, cells were fixed (with formaldehyde 2%) and stained for 10 min with 1.5% Genetian violet. 50% Tissue Culture Infective Dose (TCID50) titer was determined, for example, according to methods described in Reed, L. J., & Muench, H. (1938). L. J. Reed and H. Muench; A Simple Method of Estimating Fifty Percent Endpoints; The American journal of Hygiene Vol 27 May 1938 No. 3 493-497. The control microorganism used was MS2 including a culture of male specific-2 bacteriophage (ATCC 155597-B1) and *E. coli* MS2 bacteriophage host (ATCC 155597). MS2 stocks were prepared and stored, for example, according to the procedure outlined in the Ultraviolet Disinfection Guidance Manual 2006 ("ULTRAVIOLET DISINFECTION GUIDANCE MANUAL" EPA 815-D-03-00 7 Apr. 2006.)

The bacteriophage titer was checked once immediately after preparation, and again within 24 hours prior to the experiment. The collimated beam apparatus was operated, for example, according to the procedure outlined in the Ultraviolet Disinfection Guidance Manual. Germicidal light intensity and Petri factors were measured using OPHIR UV detector. The UV transmission (UVT) at 254 nm of the viral suspension was measured by a spectrophotometer in a 1 cm quartz cuvette.

The LP UV dose (namely, the US dose of a law pressure lamp emitting at 253.7 nm), $D_{CB}$, may be calculated according to exposure conditions (e.g., measured ultraviolet transmitting (UVT) of the microbial suspension and UV intensity of low pressure lamp). The LP UV dose, $D_{CB}$, may be calculated separately for each CBA test, for example, as follows:

$$D_{CB} = E_i P_f (1 - R) \frac{L(1 - 10^{-ad})}{(d - L) ad \ln(10)} t$$

where:
$D_{CB}$=UV dose (mJ/cm$^2$)
$E_i$=Average UV irradiance (measured before and after irradiating the sample) (milliwatts (mW)/cm$^2$)
$P_f$=Petri factor (unit-less)
R=Reflectance at the air-water interface at the irradiating wavelength (e.g., 254 nm) (unit-less)
L=Distance from the lamp centerline to the suspension surface (cm)
d=Depth of the suspension (cm)
a=UV absorption coefficient (base 10) of the suspension at the irradiating wavelength e.g., 254 nm) (cm$^{-1}$)
t=Exposure time (seconds)

LP UV doses were tested in a range of 0-120 mJ/cm$^2$ (0, 20, 40, 60, 80, 100, 120, mJ/cm$^2$) for MS2 bacteriophage and 0-250 mJ/cm$^2$ (0, 30, 60, 120, 250 mJ/cm$^2$) for IPNV. The UV lamp used in the LP-CBA was a 15 watt (W) low-pressure germicidal lamp (emitting at 253.7 nm) and the UV lamp used in the MP-CBA was a 1 kilowatt (kW) optimized medium-pressure IPV customized lamp. The samples were illuminated using two lamp powers: 100% and 25%. 20 ml samples of each viral suspension were illuminated with LP-CBA and with MP-CBA in Petri dishes (of 50 cm$^2$ surface area, 1 cm sample depth) with slow stirring. The IPNV suspension was illuminated and kept on ice during testing.

The samples were illuminated with the maximum dose to test for possible harmful effect of the solution to the IPNV. IPNV was added to the samples immediately after the illumination in the same concentration as added to the non-UV illumination sample. These samples are referred to as "medium with IPNV" in tables 1-3. Samples without IPNV were illuminated with the maximum dose to test for possible harmful effect of the solution to the cells. These samples are referred to as "medium w/o IPNV" in tables 1-3.

The concentration of each of the samples was determined using an MS2 enumeration procedure (e.g., the Pour Plate method) and IPNV plaque assay/end point titration procedure. The log inactivation may be computed, for example, as follows:

$$\log 10(No/N)$$

where:
No=Concentration of microorganisms prior to UV light exposure.
N=Concentration of microorganisms present after UV light exposure The experimental results were computed as a UV dose to log inactivation function, and a trend line equation was determined for each LP-CBA experiment.

The reduction equivalent UV dose value of MP-CBA was determined by comparing the MS2 bacteriophage's log inactivation achieved by the LP-CBA to the equal log inactivation achieved by the MP-CBA under specific condition (MP-UV exposure time, suspensions UVT at 254 nm, UV lamp power, etc.). The RED value required for inactive IPNV was determined by comparing the MS2 bacteriophage's MP-UV exposure time (with specific known RED) to MP-UV exposure time of IPNV under specific exposure conditions.

Reference is made to FIG. 4, which is a graph that plots correlations between UV doses and the inactivation of IPNV, in accordance with embodiments of the invention. FIG. 4 shows results for low pressure UV doses (listed in table 1) The results for low pressure UV doses (in FIG. 4) are from tests conducted in accordance with embodiments of the invention and from literature data (e.g., H. Liltved et al.; High resistance of fish pathogenic viruses to UV irradiation and ozonated seawater; *Aquacultural Engineering* 34 (2006) 72-82).

Table 1 lists results of the IPNV inactivation by UV light irradiated with low pressure (LP) lamps. IPNV inactivation results are measured for two strains of IPNV, ATCC no. VR1318 (isolated from Trout) and ATCC #VR-1320 (isolated from Pike fry), in two independent tests, "run 1" and "run 2," to verify results. Only samples with >25 PFU/ml may be considered viable. Disinfection may be considered optimal for a log inactivation greater than or equal to 3.

TABLE 1

LP lamp UV dose (in mJ/cm2) for IPNV inactivation

| LP UV | ATCC no. VR1318 | | ATCC no. VR1320 | |
|---|---|---|---|---|
| dose ($mJ/cm^2$) | Run I Log. Inact. | Run II Log. Inact. | Run I Log. Inact. | Run II Log. Inact. |
| 0 | 0.00 | 0.00 | 0.00 | 0.00 |
| 30 | 0.76 | 0.72 | 1.00 | 0.84 |
| 60 | 0.85 | 1.36 | 1.25 | 1.40 |
| 120 | 2.11 | 2.10 | 2.25 | 2.40 |
| 250 | 2.60 | >5.2* | >3.7* | >3.5* |
| Medium with IPNV | −0.08 | NA | 0.29 | NA |
| Medium w/o IPNV | NA | NA | 0.00 | 0.00 |

*Invalidated values

In tests conducted in accordance with embodiments of the invention, no harmful effect to the cell and to the IPNV were detected in the illuminated solutions. No significant difference was observed between the responses of the two IPNV strains, ATCC no. VR1318 and ATCC #VR-1320, when illuminated with UV light. The optimized MP UV lamp was found to be more effective for inactivating IPNV than was the LP UV lamp. In the set of CBA tests performed with the optimized medium pressure (MP) lamp for achieving an inactivation level of the IPNV between 0.2-3.3 logs reduction it was found that the optimized medium pressure lamp (MP) was more efficient by 2.2-8.6 time relative to the LP lamp Reference is made to FIG. 5, which is a graph of the relative spectra of MP UV lamps at different pressures (e.g., defined by mercury (Hg) bars). This figure shows the difference in the relative contributions of different MP Hg UV lamps to the UV effect on IPN. Contributing factors may be taken into account: (1) Variation of pressure (e.g., measured by mercury (Hg) bar) in MP lamp will cause enhancement of the specific spectral bands and (2) the material of the envelope and (3) the composition of the materials in the lamp. (1) Pressure tuning is discussed in reference to FIGS. 5, 6 and 8. (2) The material of the envelope is discussed in reference to FIGS. 9 and 10. A lamp envelope made of substantially pure silica synthetic quartz which enables higher transparency at 200-230 nm spectral range and by this the lamps emits more UV light at the range of 200-240 nm, the amount of light can be about 9% higher. (3) Changing the lamps internal chemistry e.g. by doping, may also increase IPN inactivation since the materials of the lamp affect spectral transmission of UV light. For example, the lamps may be composed of mercury e.g. doped with a metal halide additive such as Iron Halide. Such doping may cause the lamp to have higher radiation e.g. in the range of 200-230 and 260-300 nm. In addition, some embodiments may further use "electrode-less" lamps to enable more flexibility in using different lamp chemistry.

Reference is made to FIG. 6, which is a graph of the cumulative intensity of the MP lamps with different pressures. The upper line shows the cumulative intensity of a mercury lamp having 7 Hg bars pressure and the lower line shows the cumulative intensity of a mercury lamp having 1.6 Hg bars pressure. The intensities in these figures are normalized.

Reference is made to FIG. 7, which is a graph of the IPN spectral response curve, normalized at 254 nm. This graph shows that IPN is inactivated at a minimum around 254 nm. Inactivation increases exponentially by both raising and lowering the wavelength to higher and lower ranges. At the lower range (below 254 nm), inactivation of IPN increases by 17 times. At the higher range (above 254 nm), inactivation of IPN increases by 3 times. The higher range may be preferred in some embodiments because of increased water transmission of UV light at higher wavelengths.

For example, IPN is 70% more sensitive in the wavelength of 260 nm, 300% more sensitive in a wavelength of 280 nm and 1700% in a wavelength of 220 nm. Accordingly, a lamp may be used that emits UV light above 260 nm so that the needed dose will be 70% lower than one that is using a lamp of 254 nm. A UV system according to embodiments of the invention may include a lamp that emits UV light at a wavelength of approximately 220 nm to be 1700% more efficient than a system that is based on UV lamp emit UV light at a wavelength of 254 nm.

Another important parameter associated with the performance of UV system is the water transmission to UV light (UVT). Water transmission decreases as the wavelength spectrum decreases. For example, for the water of Ein Gedi illuminated at 220 nm, after 1 cm the amount of remaining intensity was 35%. At 260 nm, after 1 cm, the amount of remaining intensity was 90%. That is, 90% of the photons were still available for inactivating the IPN. Accordingly, a higher range of wavelengths may be preferred.

Reference is made to FIG. 8, which is a graph of the cumulative intensity of the MP lamps with different pressures with respect to the IPN spectral response. The upper line shows the cumulative intensity of a mercury lamp having 7 Hg bars pressure and the lower line shows the cumulative intensity of a mercury lamp having 1.6 Hg bars pressure. As shown in FIG. 6, a higher pressure MP lamp may contribute approximately 40% more to the cumulative intensity than the lower pressure MP lamp. Embodiments of the invention include a MP lamp with pressure higher than 1.6 bar and preferably, higher than 4 or 5 bar, for example, 7 bar.

Reference is made to FIG. 9, which is a summary table listing the total radian power and normalized radian power of a PS (synthetic quartz) MP lamp and a regular quartz MP lamp.

Reference is made to FIG. 10, which is a graph of the spectra of a PS (synthetic quartz) MP lamp (violet), and the regular quartz (blue). FIG. 10 shows that the difference in the IPN response sensitivity to the 200-230 nm wavelength range (TOC(200-230 nm) PS to Reg) may reach up to 9%, contributing to the overall cumulative germicidal intensity. Embodiments of the invention may include a lamp composed of pure silica synthetic quartz. Such a lamp may have a relatively high transparency at 200-230 nm spectral range.

Different embodiments are disclosed herein. Features of certain embodiments may be combined with features of other embodiments; thus certain embodiments may be combinations of features of multiple embodiments.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. A method for inactivation of Infectious Pancreatic Necrosis Virus (IPNV) comprising:

illuminating a liquid containing IPNV with a ultraviolet (UV) light emitted from a medium pressure mercury UV lamp tuned to optimize IPNV inactivation, wherein the UV light being substantially in a wavelength range between 260 and 400 nm and the UV lamp exhibits a pressure greater than 1.6 bar.

2. The method of claim 1, wherein illuminating the liquid containing the IPNV comprises illuminating the liquid with a UV dose of less than or equal to 80 mJ/cm$^2$ for 99.9% inactivation of the IPNV.

3. The method of claim 1, wherein the pressure of the lamp is greater than 3 bar.

4. The method of claim 1, wherein the pressure of the lamp is greater than 6 bar.

5. The method of claim 1, wherein the UV lamp is composed of pure silica synthetic quartz.

6. The method of claim 1, wherein the UV lamp is doped with a metal halide additive.

* * * * *